US011332786B2

(12) United States Patent
Moon (10) Patent No.: US 11,332,786 B2
(45) Date of Patent: May 17, 2022

(54) SENSOR AND SENSING SYSTEM

(71) Applicant: Illumina, Inc., San Diego, CA (US)

(72) Inventor: John Moon, Rancho Santa Fe, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 16/440,428

(22) Filed: Jun. 13, 2019

(65) Prior Publication Data
US 2020/0002758 A1 Jan. 2, 2020

Related U.S. Application Data

(60) Provisional application No. 62/692,468, filed on Jun. 29, 2018.

(30) Foreign Application Priority Data

Jul. 23, 2018 (NL) .................................. N2021376

(51) Int. Cl.
*C12Q 1/68* (2018.01)
*C12Q 1/6869* (2018.01)
(Continued)

(52) U.S. Cl.
CPC .......... *C12Q 1/6869* (2013.01); *C12N 15/10* (2013.01); *C12N 15/113* (2013.01)

(58) Field of Classification Search
CPC ............ C12Q 1/6825; C12Q 2565/607; C12Q 2565/543; C12Q 1/6869; C12Q 2563/116;
(Continued)

(56) References Cited

U.S. PATENT DOCUMENTS 7,176,482 B1 * 2/2007 Ben-Jacob ............. B82Y 10/00
257/30
2002/0072054 A1 6/2002 Miles et al.
(Continued)

FOREIGN PATENT DOCUMENTS

CN 102384934 3/2012
KR 101220869 1/2013
(Continued)

OTHER PUBLICATIONS

Holzel et al "Oriented and vectorial immobilization of linear M13 DNA between interdigitated electrodes—towards single molecule DNA nanostructures" Biosensor and Bioelectronics, 2003, 18:555-564. (Year: 2003).*

(Continued)

*Primary Examiner* — Betty J Forman
(74) *Attorney, Agent, or Firm* — Illumina, Inc.

(57) ABSTRACT

A sensor includes two electrodes and a modulatable electrically conductive channel attached to the two electrodes. The modulatable electrically conductive channel includes a modified, partially double stranded nucleic acid polymer electrically connected to the two electrodes and bridging the space between the two electrodes. The modified, partially double stranded nucleic acid polymer includes two polynucleotide chains partially bonded together, a gap in a first of the polynucleotide chains wherein nucleotide bases are missing, and a plurality of nucleotide bases of a second of the polynucleotide chains exposed at the gap in the first of the polynucleotide chains.

19 Claims, 5 Drawing Sheets

Specification includes a Sequence Listing.

(51) Int. Cl.
*C12N 15/10* (2006.01)
*C12N 15/113* (2010.01)

(58) Field of Classification Search
CPC ........ C12Q 2521/101; C12Q 2525/113; C12N 5/10; C12N 15/10; C12N 15/113; G01N 33/5438; G01N 27/3276; G01N 27/3278; G01N 27/4145; G01N 27/4146; B01L 2300/0645; B82Y 10/00; F41H 11/12; G11C 13/0014; G11C 13/0019

See application file for complete search history.

(56) References Cited

U.S. PATENT DOCUMENTS

| | | | | |
|---|---|---|---|---|
| 2003/0203394 | A1* | 10/2003 | Eichen | G01N 33/5438 435/6.18 |
| 2004/0146863 | A1* | 7/2004 | Pisharody | G11C 13/0014 435/6.11 |
| 2004/0209355 | A1* | 10/2004 | Edman | B82Y 20/00 435/287.2 |
| 2006/0146323 | A1 | 7/2006 | Bratkovski et al. | |
| 2006/0246497 | A1 | 11/2006 | Huang et al. | |
| 2010/0101956 | A1 | 4/2010 | Choi et al. | |
| 2010/0184062 | A1* | 7/2010 | Steinmuller-Nethl | C12Q 1/6825 435/6.19 |
| 2013/0303404 | A1 | 11/2013 | Connolly | |
| 2013/0310548 | A1 | 11/2013 | Park | |
| 2017/0044605 | A1* | 2/2017 | Merriman | G01N 27/3276 |

FOREIGN PATENT DOCUMENTS

| | | |
|---|---|---|
| RU | 25328552 | 11/2014 |
| TW | 200637916 | 11/2006 |
| WO | 2000/060125 | 10/2000 |
| WO | 2009003208 A1 | 1/2009 |
| WO | 2010/132727 | 11/2010 |
| WO | 2016/010975 | 1/2016 |
| WO | 2017/189930 | 11/2017 |
| WO | WO-2017189930 A1 * | 11/2017 ....... C12Q 2521/543 |

OTHER PUBLICATIONS

Artés, J.M., et al., "Conformational gating of DNA conductance," Nature Communications, Dec. 9, 2015, 6:8870.
Xiang, L, et al., "Gate-controlled conductance switching in DNA," Nature Communications, Feb. 20, 2017, 8:14471.

* cited by examiner

SEQUENCE LISTING

<160> NUMBER OF SEQ ID NOS: 1

<210> SEQ ID NO 1
<211> LENGTH: 21
<212> TYPE: DNA
<213> ORGANISM: Artificial Sequence
<220> FEATURE:
<223> OTHER INFORMATION: Conductivity Sensor

<400> SEQUENCE: 1
tgggccccat cccccctagg c                21

SENSOR AND SENSING SYSTEM

CROSS-REFERENCE TO RELATED APPLICATIONS

This application claims the benefit of U.S. Provisional Application Ser. No. 62/692,468, filed Jun. 29, 2018, and Netherland Application Serial Number N2021376, filed Jul. 23, 2018; the content of each of which is incorporated by reference herein in its entirety.

REFERENCE TO SEQUENCE LISTING

The Sequence Listing submitted herewith via EFS-Web is hereby incorporated by reference in its entirety. The name of the file is ILI149B_IP-1687-US_sequence_listing_ST25.txt, the size of the file is 366 bytes, and the date of creation of the file is Jun. 7, 2019.

BACKGROUND

Various protocols in biological or chemical research involve performing a large number of controlled reactions on local support surfaces or within predefined reaction chambers. The designated reactions may then be observed or detected and subsequent analysis may help identify or reveal properties of chemicals involved in the reaction. For example, in some multiplex assays, an unknown analyte having an identifiable label (e.g., fluorescent label) may be exposed to thousands of known probes under controlled conditions. Each known probe may be deposited into a corresponding well of a microplate. Observing any chemical reactions that occur between the known probes and the unknown analyte within the wells may help identify or reveal properties of the analyte. Other examples of such protocols include known DNA sequencing processes, such as sequencing-by-synthesis (SBS) or cyclic-array sequencing. With polynucleotide sequencing techniques, the analysis may help identify or reveal properties of the polynucleotide involved in the reactions.

INTRODUCTION

A first aspect disclosed herein is a sensor. In an example, the sensor comprises two electrodes having a space therebetween; and a modulatable electrically conductive channel attached to the two electrodes, the modulatable electrically conductive channel including a modified, partially double stranded nucleic acid polymer electrically connected to the two electrodes and bridging the space between the two electrodes, the modified, partially double stranded nucleic acid polymer including: two polynucleotide chains partially bonded together; a gap in a first of the polynucleotide chains wherein nucleotides are missing; and a plurality of nucleotide bases of a second of the polynucleotide chains exposed at the gap in the first of the polynucleotide chains.

In an example of the sensor, the gap has a length ranging from about 10 nm to about 50 nm.

An example of the sensor further comprises a polymerase attached to the modified, partially double stranded nucleic acid polymer.

In an example of the sensor, i) linkers respectively attach each end of the first of the polynucleotide chains to a respective one of the two electrodes; or ii) linkers respectively attach each end of the second of the polynucleotide chains to a respective one of the two electrodes; or iii) both i and ii.

In an example of the sensor, at least one of the plurality of nucleotide bases exposed at the gap is a guanine base.

In an example of the sensor, each of the plurality of nucleotide bases exposed at the gap is a guanine base.

An example of the sensor further comprises a detector to detect a response from the modified, partially double stranded nucleic acid polymer when a switch strand, including a strand of nucleotides including bases complementary to at least some of the plurality of nucleotide bases exposed at the gap, associates with the at least some of the plurality of nucleotide bases at the gap.

An example of the sensor further comprises a substrate supporting the two electrodes; and a polymerase attached to the substrate.

An example of the sensor further comprises a fluidic system to introduce a reagent to the modified, partially double stranded nucleic acid polymer. In an example, the reagent includes labeled nucleotides, at least one of the labeled nucleotides including: a nucleotide; a linking molecule attached to a phosphate group of the nucleotide; and a switch strand attached to the linking molecule, the switch strand including a strand of nucleotides including bases complementary to at least some of the plurality of nucleotide bases exposed at the gap.

An example of the sensor further comprises a plurality of other modulatable electrically conductive channels attached to the two electrodes, each of the other modulatable electrically conductive channels including a respective modified, partially double stranded nucleic acid polymer electrically connected to the two electrodes and bridging the space between the two electrodes.

In an example of the sensor, the modulatable electrically conductive channel exhibits a first conductance when the plurality of nucleotide bases are exposed at the gap; and a second conductance that is different than the first conductance when at least some of the plurality of nucleotide bases at the gap are associated with complementary nucleotide bases.

It is to be understood that any features of the sensor disclosed herein may be combined together in any desirable manner and/or configuration, and/or with any other example disclosed herein.

A second aspect disclosed herein is a labeled nucleotide, comprises a nucleotide; a linking molecule attached to a phosphate group of the nucleotide; and a switch strand attached to the linking molecule, the switch strand including a strand of nucleotides including bases complementary to at least some of the plurality of nucleotide bases exposed at the gap of the sensor of the first aspect.

A third aspect disclosed herein is a kit, comprising: an electronic component, including: a support; and two electrodes operatively disposed on the support and separated by a space; and a polymeric solution, including: a liquid carrier; and a modified, partially double stranded nucleic acid polymer in the liquid carrier, the modified, partially double stranded nucleic acid polymer including: two polynucleotide chains partially bonded together and having opposed ends; a linker attached to each of the opposed ends, each linker to attach to a respective one of the two electrodes; a gap in a first of the polynucleotide chains wherein nucleotides are missing; and a plurality of nucleotide bases of a second of the polynucleotide chains exposed at the gap in the first of the polynucleotide chains; the modified, partially double stranded nucleic acid polymer to form a modulatable electrically conductive channel in the space between the two electrodes when each linker attaches to the respective one of the two electrodes.

In an example, the kit further comprising a reagent solution including labeled nucleotides, at least one of the labeled nucleotides including: a nucleotide; a linking molecule attached to a phosphate group of the nucleotide; and a switch strand attached to the linking molecule, the switch strand including a strand of nucleotides including bases complementary to at least some of the plurality of nucleotide bases exposed at the gap. In an example of the kit, the bases in the switch strand are completely complementary to the plurality of nucleotide bases exposed at the gap. In another example of the kit, the switch strand further includes at least one nucleotide having a mismatched base that is non-complementary to a corresponding one of the plurality of nucleotide bases exposed at the gap. In still another example of the kit, the strand of nucleotides in the switch strand has at least one nucleotide fewer than the plurality of nucleotide bases exposed at the gap. In yet a further example of the kit, the strand of nucleotides in the switch strand has a higher number of nucleotides than the plurality of nucleotide bases exposed at the gap, and wherein a portion of the switch strand forms a stem loop when associated at the gap. In an example of the kit, the strand of nucleotides in the switch strand has a higher number of nucleotides than the plurality of nucleotide bases exposed at the gap; a portion of the switch strand forms a stem loop when associated at the gap; and another portion of the switch strand is completely complementary to the plurality of nucleotide bases exposed at the gap or includes at least one nucleotide having a mismatched base that is non-complementary to a corresponding one of the plurality of nucleotide bases exposed at the gap.

It is to be understood that any features of the kit may be combined together in any desirable manner. Moreover, it is to be understood that any combination of features of the kit and/or of the sensor and/or of the labeled nucleotide may be used together, and/or combined with any of the examples disclosed herein.

In a fourth aspect, a sensing system comprises a flow cell; and an electronic sensor integrated into the flow cell, the electronic sensor including: two electrodes having a space therebetween; a modulatable electrically conductive channel attached to the two electrodes, the modulatable electrically conductive channel including a modified, partially double stranded nucleic acid polymer electrically connected to the two electrodes and bridging the space between the two electrodes, the modified, partially double stranded nucleic acid polymer including: two polynucleotide chains partially bonded together; a gap in a first of the polynucleotide chains wherein nucleotides are missing; and a plurality of nucleotide bases of a second of the polynucleotide chains exposed at the gap in the first of the polynucleotide chains.

In an example, the sensing system further comprises a reagent delivery system to selectively introduce a reagent to an input of the flow cell. In an example, the reagent is in a sample container, the reagent including labeled nucleotides, at least one of the labeled nucleotides including: a nucleotide; a linking molecule attached to a phosphate group of the nucleotide; and a switch strand attached to the linking molecule, the switch strand including a strand of nucleotides including bases complementary to at least some of the plurality of nucleotide bases exposed at the gap.

An example of the sensing system further comprises a detector to detect a response from the electronic sensor.

An example of the sensing system further comprises a polymerase anchored to the modified, partially double stranded nucleic acid polymer or a support of the electronic sensor; and a template polynucleotide chain to be introduced to the electronic sensor.

It is to be understood that any features of the sensing system may be combined together in any desirable manner. Moreover, it is to be understood that any combination of features of the sensing system and/or of the sensor, and/or of the kit and/or of the labeled nucleotide may be used together, and/or combined with any of the examples disclosed herein.

A fifth aspect disclosed herein is a method. In an example, the method comprises introducing a template polynucleotide chain to an electronic sensor having a polymerase tethered to i) a modulatable electrically conductive channel that bridges a space between, and is electrically connected to two electrodes or ii) a substrate supporting the two electrodes, the modulatable electrically conductive channel including a modified, partially double stranded nucleic acid polymer, which includes: two polynucleotide chains partially bonded together; a gap in a first of the polynucleotide chains wherein nucleotides are missing; and a plurality of nucleotide bases of a second of the polynucleotide chains exposed at the gap in the first of the polynucleotide chains; introducing reagents including labeled nucleotides to the electronic sensor, whereby a nucleotide of one of the labeled nucleotides associates with the polymerase and a nucleotide-specific switch strand of the one of the labeled nucleotides associates with at least some of the plurality of nucleotide bases exposed at the gap; and in response to the association at the gap, detecting a response of the electronic sensor.

An example of the method further comprises associating the response of the electronic sensor with the associated nucleotide-specific switch strand; and based on the associated nucleotide-specific switch strand, identifying the nucleotide of the one of the labeled nucleotides.

An example of the method further comprises heating to disassociate the nucleotide-specific switch strand from the gap.

It is to be understood that any features of the method may be combined together in any desirable manner. Moreover, it is to be understood that any combination of features of the method and/or of the sensing system and/or of the sensor and/or any of the kits and/or of the labeled nucleotide may be used together, and/or combined with any of the examples disclosed herein.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

An electronic/electrical sensor is disclosed herein which may be used for single molecule detection in nucleic acid sequencing procedures. The sensor includes a modulatable electrically conductive channel electrically attached to two electrodes. The modulatable electrically conductive channel includes a modified, partially double stranded nucleic acid polymer (referred to herein as the modified "dsNA"), and thus may be referred to as a conductive molecular nanowire. One polynucleotide chain or strand of the modified dsNA has a gap where nucleotide bases are exposed. The other of the polynucleotide chains or strands extends from one of the electrodes to the other of the electrodes, and thus the modulatable electrically conductive channel provides a conduction path between the two electrodes even when the nucleotide bases at the gap are exposed (and single molecule detection is not taking place). The nucleotide bases at the gap are able to associate with a switch strand having at least some nucleotide bases complementary to the nucleotide bases at the gap. When the switch strand associates at the gap, the conduction path increases and the conductance of the electrically conductive channel is modulated. As such, the modulatable electrically conductive channel exhibits a first conductance when the plurality of nucleotide bases are exposed at the gap; and a second conductance that is different than the first conductance when at least some of the plurality of nucleotide bases at the gap are associated with complementary nucleotide bases. In an example, when the nucleotide bases at the gap are exposed, the conductivity of the modulatable electrically conductive channel is relatively low. In contrast, when the switch strand associates at the gap, the conductivity of the modulatable electrically conductive channel changes (e.g., increases or decreases), in some instances, by orders of magnitude.

The switch strand may be part of a labeled nucleotide, which includes a specific nucleotide linked to the switch strand. As the specific nucleotide is being incorporated into a nascent strand during a nucleic acid sequencing procedure, the switch associates at the gap, which results in a conductivity change of the modulatable electrically conductive channel. Since the nucleotide and the switch strand are specific to one another, the conductivity change associated with the switch is also associated with the nucleotide. As such, the change in conductivity may be used to identify the nucleotide base being incorporated into the nascent strand.

Figure 1A:
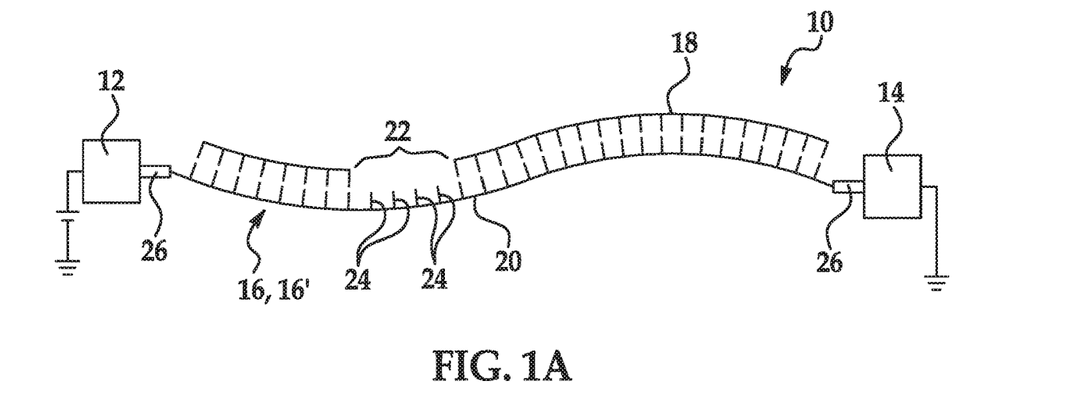
FIG. 1A is a schematic diagram of an example of a sensor disclosed herein.

Referring now to FIG. 1A, an example of the sensor 10 is depicted. The example sensor 10 is an electrical/electronic sensor. The sensor 10 includes two electrodes 12, 14 having a space therebetween, and a modulatable electrically conductive channel 16 attached to the two electrodes 12, 14. The modulatable electrically conductive channel includes a modified, partially double stranded nucleic acid polymer (i.e., modified dsNA) 16' electrically connected to the two electrodes 12, 14 and bridging the space between the two electrodes 12, 14, the modified dsNA 16' including two polynucleotide chains 18, 20 partially bonded together; a gap 22 in a first of the polynucleotide chains 18 wherein nucleotides are missing; and a plurality of nucleotide bases 24 of a second of the polynucleotide chains 20 exposed at the gap 22 in the first of the polynucleotide chains 18.

The electrodes 12, 14 are in electrical communication with the modified dsNA 16'/modulatable electrically conductive channel 16, and thus a constant conduction path exists between the electrodes 12, 14 when the sensor 10 is in operation. As mentioned, this conduction path is modulatable by the association of a switch strand at the gap 22.

Any suitable electrode material may be used that can chemically and electrically attach to the modified dsNA 16'. Examples of suitable electrode materials include gold, platinum, carbon, indium tin oxide, etc.

The modified dsNA 16' is a nucleic acid polymer which includes two polynucleotide chains 18, 20 partially bonded together. By "partially bonded together", it is meant that some of the nucleotide bases of the two chains 18, 20 are hydrogen bonded to one another to form a double helix, but that one of the chains 18 has a gap 22 without any nucleotides. At the gap 22 in the one chain 18, the nucleotide bases of the other of the chains 20 are exposed. By "exposed", it is meant that the bases of these nucleotides are not bonded to another nucleotide, and thus are available to be bound, hybridized, or otherwise associated with complementary nucleotides.

Figure 5:
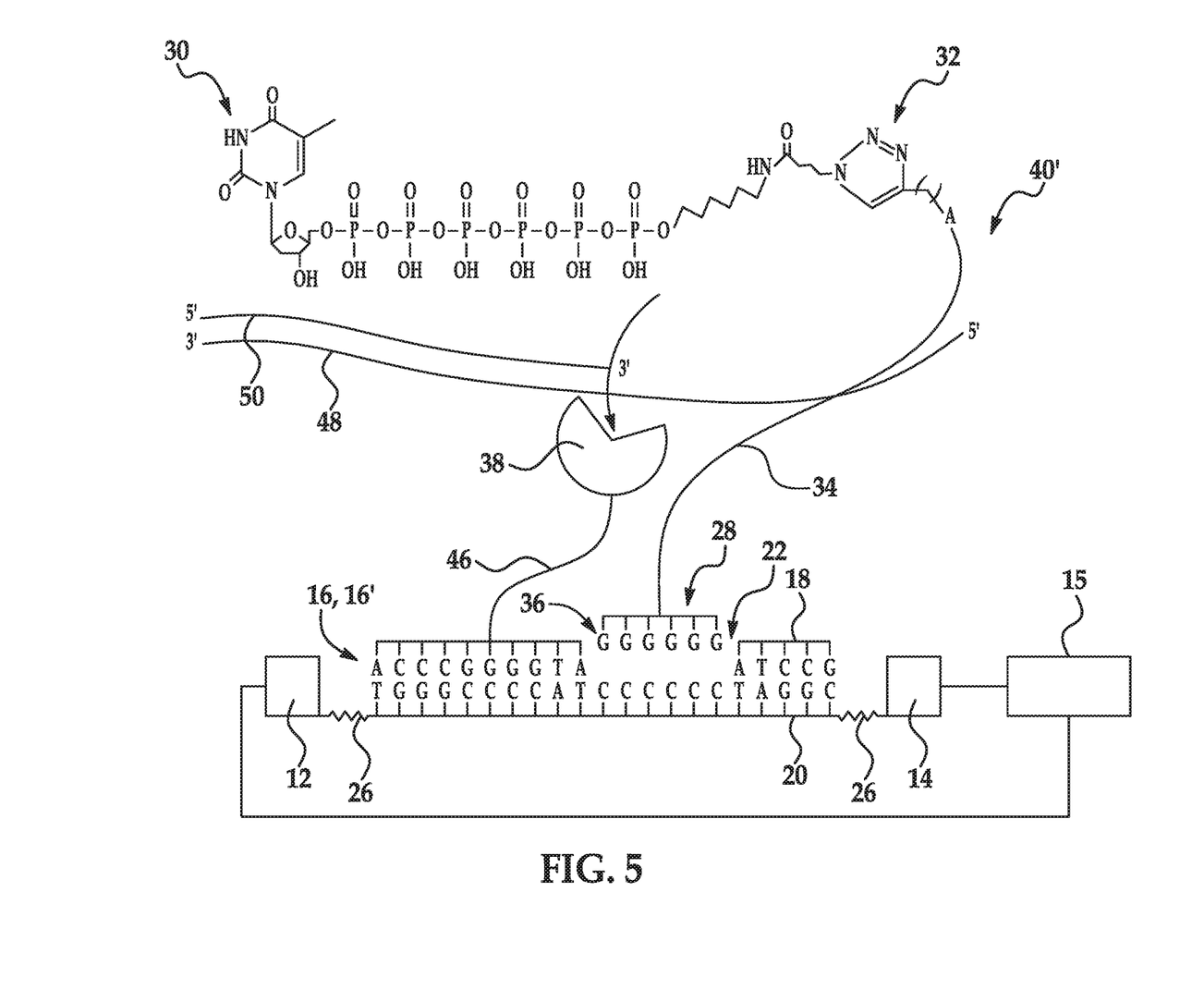
FIG. 5 is a schematic diagram of an example of a sensing system.

The nucleotides of the two polynucleotide chains 18, 20 may be natural nucleotides. Natural nucleotides include a nitrogen containing heterocyclic base, a sugar, and one or more phosphate groups. Examples of natural nucleotides of the two polynucleotide chains 18, 20 include ribonucleotides or deoxyribonucleotides. In ribonucleotides, the sugar is a ribose, and in deoxyribonucleotides, the sugar is a deoxyribose, i.e. a sugar lacking a hydroxyl group that is present at the 2' position in ribose. In an example, the nucleotide is in the polyphosphate form because it includes several phosphate groups (e.g., tri-phosphate (i.e., gamma phosphate), tetra-phosphate, penta-phosphate, hexa-phosphate (as shown in FIG. 5), etc.). The heterocyclic base (i.e., nucleobase) can be a purine base or a pyrimidine base or any other nucleobase analog. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine. The polynucleotide chains 18, 20 may also include any nucleic acid analogs. A nucleic acid analog may have any of the phosphate backbone, the sugar, or the nucleobase altered. Examples of nucleic acid analogs include, for example, universal bases or phosphate-sugar backbone analogs, such as peptide nucleic acid (PNA).

As mentioned herein, the first polynucleotide chain 18 has a gap 22 where nucleotides are not present. The gap 22 may be located anywhere along the chain 18, for example, at or near the center, at either end of the chain 18, between the center and one end of the chain 18, etc. As such, in some examples, the first polynucleotide chain 18 includes two shorter chains separated by the gap 22. In other examples (e.g., when the gap 22 is at either end of the chain 18), the first polynucleotide chain 18 is a single continuous chain. In still other examples, the first polynucleotide chain 18 may have multiple gaps 18 along the polymer backbone. The gap(s) 22 may have any length that is shorter than the total length of the dsNA 16'. In an example, the length of each gap 22 ranges from about 5 nm to about 60 nm. In another example, the length of each gap 22 ranges from about 10 nm to about 50 nm. In still another example, the length of each gap 22 ranges from about 20 nm to about 40 nm. While the length of the gap 22 is set forth as a metric unit, it is to be understood that the gap length may also be defined in terms of the number of nucleotides that could fit into the gap 22, or the number of nucleotide bases of the second polymeric chain 20 that are exposed at the gap 22. The gap(s) 22 in the first polynucleotide chain 18 reduces the conductivity of the modified dsNA 16'.

At the gap 22 in the first polynucleotide chain 18, a plurality of nucleotides of the second polymeric chain 20 are exposed. In particular, the bases 24 of these nucleotides are exposed. The exposed bases 24 may all be the same bases or may be a combination of different bases. In an example, at least one of the exposed bases 24 is guanine (G). In this example, the other exposed bases 24 may be any one of or any combination of adenine (A), cytosine (C), thymine (T), and/or uracil (U). In another example, each of the exposed bases 24 is guanine (G). It may be desirable to include several guanine (G) bases in a row exposed at the gap 22, as the guanine (G) bases conduct electricity better than the other bases.

The two, partially bonded polynucleotide chains have opposed ends, and a linker may be attached to each of the opposed ends. In the examples disclosed herein, i) linkers respectively attach each end of the first of the polynucleotide chains 18 to a respective one of the two electrodes 12, 14; or ii) linkers respectively attach each end of the second of the polynucleotide chains to a respective one of the two electrodes; or iii) both i and ii. While FIG. 1 illustrates the second polynucleotide chain 20 bonded to the electrodes 12, 14 through the linkers 26, it is to be understood that the first polynucleotide chain 18 or both chains 18, 20 may be bonded to the electrodes 12, 14 through respective linkers 26. As such, the respective 5' and 3' ends of the first and/or the second polynucleotide chain 18, 20 may have a linker 26 attached thereto. The linkers 26 electrically connected the modified dsNA 16' to the electrodes 12, 14. The linkers 26 may also be capable of chemically bonding to the respective electrodes 12, 14, thus bridging the modified dsNA 16' between the electrodes 12, 14. Therefore, the linkers 26 may depend upon the electrode material. As examples, thiolate or amine linkers may attach to gold electrodes, thiol linkers may attach to platinum electrodes, and silane linkers (e.g., azido silane) may attach to ITO electrodes. The attachment of the respective linker 26 to one of the electrodes 12, 14 may be through covalent bonding, coordination bonding, or another chemical or physical bond, depending upon the linker and the electrode material. The linkers 26 are also electrically conductive so that the conduction path between the electrodes 12, 14 is established when the modified dsNA 16' is attached to each of the electrodes 12, 14.

Any example of the sensor 10 disclosed herein may include a plurality of other modulatable electrically conductive channels 16 attached to the two electrodes 12, 14, each of the other modulatable electrically conductive channels 16 including a respective modified, partially double stranded nucleic acid polymer 16' electrically connected to the two electrodes 12, 14, and bridging the space between the two electrodes 12, 14. In other words, the sensor 10 may include two or more partially double stranded nucleic acid polymers 16', where each modified dsNA 16' is electrically connected to the two electrodes 12, 14. Multiple channels 16 are relative easy to fabricate (by allowing multiple modified dsNA 16' strands to attach), and provide several gaps 22 with which the switch strand(s) can associate. With multiple channels 16, the base signal (e.g., when no switch strand(s) are associated with the gap(s) 33 is higher, and when respective switch strands associate with the multiple modulatable electrically conductive channels 16, the detected signal may be enhanced.

While not shown in FIG. 1A, the sensor 10 may also include a substrate or support upon which the electrodes 12, 14 are positioned. An example of the support/substrate 13 is shown in FIG. 1C. The support/substrate 13 may be any solid surface upon which the electrodes 12, 14 can sit. Any non-conductive or semi-conductive solid surface may be used. The solid surface may also be non-permeable of, and inert to liquids, reagents, etc. used in a single molecule sequencing operation. Some examples of suitable supports/substrates 13 include epoxy siloxane, glass and modified or functionalized glass, plastics (including acrylics, polystyrene and copolymers of styrene and other materials, polypropylene, polyethylene, polybutylene, polyurethanes, polytetrafluoroethylene (such as TEFLON® from Chemours), cyclic olefins/cyclo-olefin polymers (COP) (such as ZEONOR® from Zeon), polyimides, etc.), nylon, ceramics/ceramic oxides, silica, fused silica, or silica-based materials, aluminum silicate, silicon and modified silicon (e.g., boron doped p+ silicon), silicon nitride ($Si_3N_4$), silicon oxide ($SiO_2$), tantalum pentoxide ($TaO_5$) or other tantalum oxide(s) ($TaO_x$), hafnium oxide ($HaO_2$), inorganic glasses, or the like. The support or substrate 13 may also be glass or silicon, with a coating layer of silicon dioxide or tantalum oxide or another ceramic oxide at the surface.

Figure 1B:
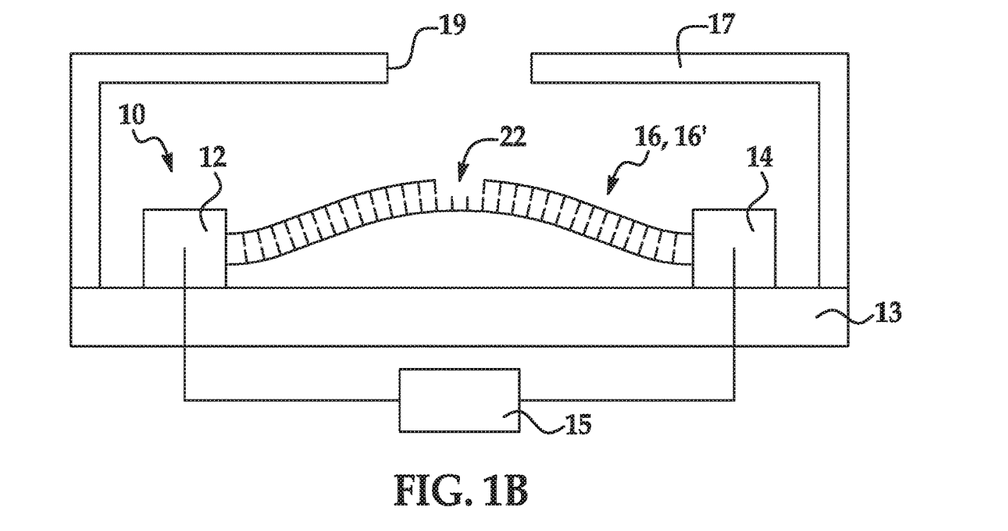
FIG. 1B is a schematic diagram of an example of a sensor and an example of a fluidic system to introduce a reagent to a modified, partially double stranded nucleic acid polymer of the sensor.
Figure 4:
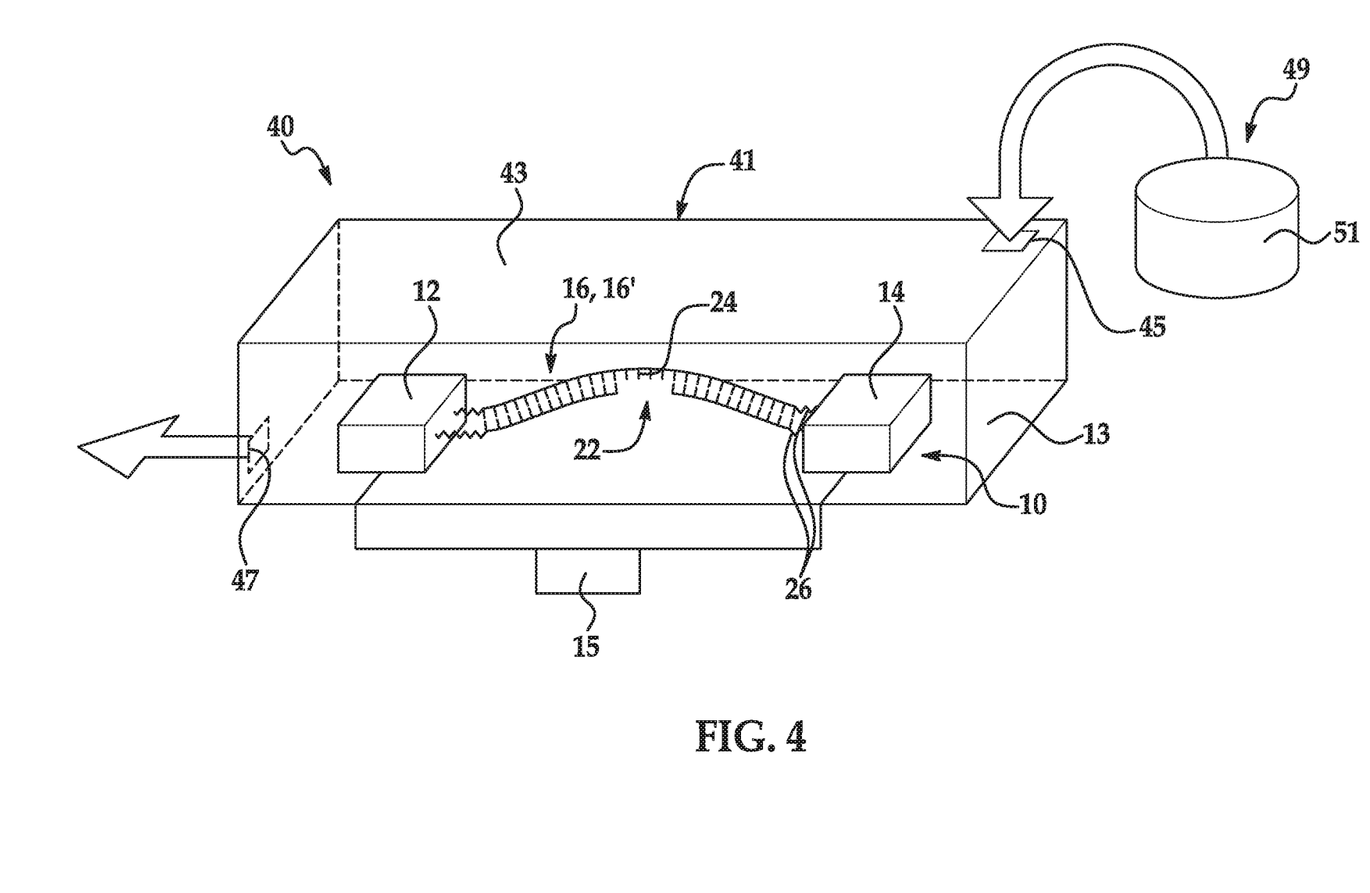
FIG. 4 is a schematic, perspective diagram of an example of a sensing system including a flow cell and an example of the sensor disclosed herein.

Also while not shown in FIG. 1A, the sensor 10 may also include a detector that can detect an electrical response of the sensor 10. Examples of the detector 15 are shown in FIGS. 1B, 4, and 5. In an example, the detector 15 is an ammeter. As will be described in more detail with reference to FIG. 5, the conductivity of the modified dsNA 16' (and thus the modulatable electrically conductive channel 16) may increase when a switch strand 28 (shown in FIG. 2), including a strand of nucleotides including bases complementary to at least some of the plurality of nucleotide bases 24 exposed at the gap 22, associates with the at least some of the plurality of nucleotide bases 24 at the gap 22.

As shown in FIG. 1B, the sensor 10 may further include a fluidic system 17 to introduce a reagent to the modulatable electrically conductive channel 16. This fluidic system 17 may be any fluidic device that can deliver the reagent to the dsNA 16', or that enables the reagent to be contained within proximity of the dsNA 16'. As shown in FIG. 1B, the fluidic system 17 may be a flow cell lid that can be attached to and removed from the support/substrate 13. This example of the fluidic system 17 includes an inlet 19 through which the reagent may be introduced. The walls of this fluidic system maintain the reagent within proximity of the dsNA 16'. As another example (not shown), the fluidic system 17 may be a pipette (or other delivery device) that can be used to deliver the reagent to the modulatable electrically conductive channel 16/dsNA 16'. In this example, the support/substrate 13 may have a trench adjacent to the modulatable electrically conductive channel 16/dsNA 16' that can receive the reagent and enable the reagent to contact the modulatable electrically conductive channel 16/dsNA 16'. While some example fluidic systems have been provided, it is to be understood that the sensor 10 may include any fluidic system 17 that can deliver a reagent to the modulatable electrically conductive channel 16/dsNA 16', and/or that enables the reagent to be contained within proximity of the modulatable electrically conductive channel 16/dsNA 16'.

The sensor 10 disclosed herein may enable single-molecule sensitivity. Moreover, when arranged in an array (i.e., several sensors 10 positioned on a substrate/support 13), very small inter-sensor distances may be used so that the density (i.e., sensor/area) can be very high.

To form the sensor 10, any suitable methods may be used. In an example, the modified dsNA 16' may be synthesized, and then the modified dsNA 16' may be attached to the electrodes 12, 14 to form the modulatable electrically conductive channel 16 in the space between the two electrodes 12, 14.

The modified dsNA 16' may be made by synthesizing the second polynucleotide chain 20, and then mixing the second polynucleotide chain 20 with complementary strand(s) that will attach to the second polynucleotide chain 20 at appropriate position(s). The mixture may then be annealed to initiate the attachment. In an example, two complementary strands may attach to respective portions of the second polynucleotide chain 20 so that the gap 22 is formed somewhere between the two ends of the resulting modified dsNA 16'. In another example, one complementary strand that is shorter than the second polynucleotide chain 20 may attach to a portion of the second polynucleotide chain 20 so that the gap 22 is formed at one end of the resulting modified dsNA 16'. It is to be understood that the second polynucleotide chain 20 and the complementary strand(s) that attach to form the first polynucleotide chain 18 may be selected to control the length of the gap 22 and the nucleotide bases 24 that are exposed at the gap 22.

The modified dsNA 16' may then be attached to the electrodes 12, 14. The linkers 26 may be attached to the modified dsNA 16' using any suitable technique, and then the linkers 26 may be attached to the electrodes 12, 14. In an example, thiol-modified DNA bases may be conjugated at the 3' and 5' ends of the chains 18, 20. In an example, the modified dsNA 16' may be immobilized on the electrodes 12, 14 by exposing the electrodes 12, 14 in a solution of the modified dsNA 16' for a suitable time, followed by rinsing with a suitable buffer to remove non-bound modified dsNA 16'.

In a method of making of making sensor 10, the electrodes 12, 14 may also be electrically connected to the detector 15.

In some examples, the sensor 10 may come pre-assembled.

In other examples, the sensor components may be part of a kit, and the kit components may be used to assemble the sensor 10. An example of the kit includes an electronic component and a polymeric solution. The electronic component includes the support 13 and two electrodes 12, 14 operatively disposed on the support and separated by a space. By "operatively disposed", it is meant that the electrodes 12, 14 may be connected to electronic circuitry that enables their operation (e.g., once hooked up to a detector 15 and power supply). The electronic circuitry may be electrically connectable to the detector 15 and to the power supply. The polymeric solution includes a liquid carrier and a modified dsNA 16' in the liquid carrier, where the modified dsNA 16' is any of the examples described herein. As described herein, the modified dsNA 16' includes the two polynucleotide chains 18, 20 partially bonded together and having opposed ends. The modified dsNA 16' may have linkers 26 attached to one or both strands 18 and/or 20 at each of the opposed ends. In an example, the modified dsNA 16' is in an ionic salt buffer solution, such as saline citrate at milli-molar to molar concentrations.

When using the kit, a user can deposit the polymer solution on the electronic components, allow the polymer solution to remain on the electronic components for a suitable time for the linkers 26 to attach to the respective electrodes 12, 14, and then the electronic component may be rinsed with a suitable buffer to remove non-bound modified dsNA 16'.

In addition to containing components to form the sensor 10, some examples of the kit may also include a reagent solution that is to be used with the sensor 10. The reagent solution includes labeled nucleotides, which are described in reference to FIG. 2.

Figure 2:
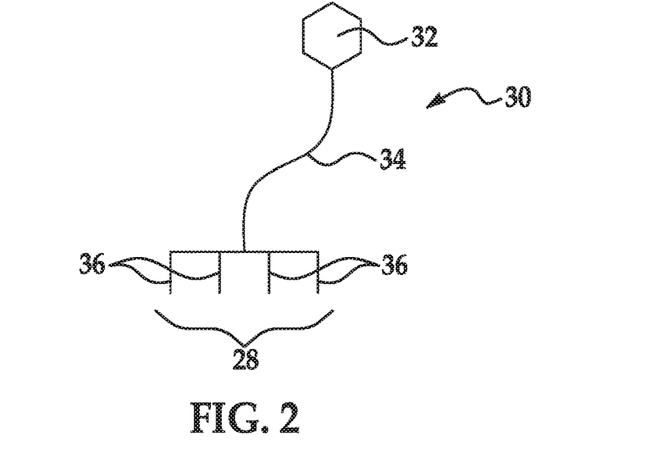
FIG. 2 is a schematic diagram of an example of a labeled nucleotide disclosed herein.

Referring now to FIG. 2, an example of a labeled nucleotide 30, which includes the switch strand 28 mentioned above, is depicted. The labeled nucleotide 30 includes a nucleotide 32, a linking molecule 34 attached to a phosphate group of the nucleotide 22, and the switch strand 28 attached to the linking molecule 34, the switch strand 28 including a strand of nucleotides including bases 36 complementary to at least some of the plurality of nucleotide bases 24 exposed at the gap 22 of the sensor 10. The labeled nucleotide 30 may be considered a non-natural or synthetic nucleotide because it is structurally or chemically distinct from a natural nucleotide.

The nucleotide 32 of the labeled nucleotide 30 may be a natural nucleotide. Natural nucleotides include a nitrogen-containing heterocyclic base, a sugar, and three or more phosphate groups. Examples of natural nucleotides include, for example, ribonucleotides or deoxyribonucleotides. As mentioned above, in a ribonucleotide, the sugar is a ribose, and in a deoxyribonucleotide, the sugar is a deoxyribose. In an example, the nucleotide 32 is in the polyphosphate form because it includes several phosphate groups (e.g., tri-phosphate, tetra-phosphate, penta-phosphate, hexa-phosphate, etc.). The heterocyclic base (i.e., nucleobase) can be a purine base (e.g., adenine (A) or guanine (G)) or a pyrimidine base (e.g., cytosine (C), thymine (T), and uracil (U)).

The labeled nucleotide 30 also includes the linking molecule 34. The linking molecule 34 may be any long chain molecule that can chemically bond, at one end, to the phosphate group(s) of the nucleotide 32 and that can chemically bond, at the other end, to the switch strand 28. The linking molecule 34 may also be selected so that it will not interact with a polymerase 38 used in the system 40, 40' (see FIGS. 4 and 5) disclosed herein. The linking molecule 34 is selected so that it is long enough to permit the switch strand 28 to associate with the nucleotide bases 24 exposed at the gap 22 of the electrical sensor 10 while, for example, the nucleotide 32 is held by the polymerase 38.

As examples, the linking molecule 34 may include an alkyl chain, a poly(ethylene glycol) chain, an amido group, a phosphate group, a heterocycle such as a triazole, nucleotides, or combinations thereof. Examples of the alkyl chain may include at least 6 carbon atoms and examples of the poly(ethylene glycol) chain may include at least 3 ethylene glycol units.

The following example illustrates an example of the labeled nucleotide 30, where the linking molecule 34 comprises an alkyl chain, an amide group, a poly(ethylene glycol) chain, and a triazole:

The following example illustrates another example of the labeled nucleotide 30, where the linking molecule 34 comprises alkyl chains, an amide group, poly(ethylene glycol) chains, a triazole, and a phosphate group:

The following example illustrates yet another example of the labeled nucleotide 30, where the linking molecule 34 comprises alkyl chains, amide groups, poly(ethylene glycol) chains, a triazole, and a phosphate group:

The following example illustrates still a further example of the labeled nucleotide 10, where the linking molecule 14, 14' comprises an alkyl chains, an amide group, poly(ethylene glycol) chains, a triazole, a phosphate group and a polynucleotide chain:

While several example linking molecules 34 have been described, it is to be understood that other linking molecules 34 may be used.

The switch strand 28 is a strand of nucleotides. The nucleotides in the switch strand 28 are similar to the nucleotide 32, i.e., they include the nitrogen containing heterocyclic base, the sugar, and three or more phosphate groups. At least some of the nucleotides in the switch strand 28 include bases 36 that are complementary to the bases 24 that are exposed at the gap 22 of the sensor 10. As such, the sequence of the nucleotides in the switch strand 28 depends, at least in part, on the sequence of the exposed bases 24.

Figure 3A:
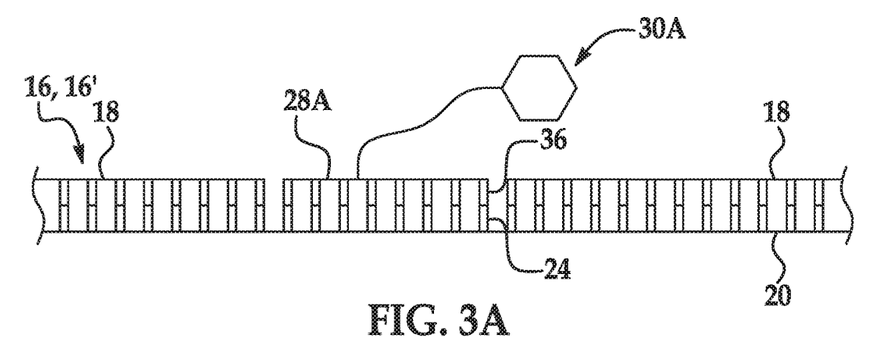
FIGS. 3A through 3D are cutaway schematic diagrams of different example labeled nucleotides, including different switch strands, associated with nucleotide bases exposed at a gap of a modified, partially double stranded nucleic acid polymer.

In one example, the bases 36 in the switch strand 28 are completely complementary to the plurality of nucleotide bases 24 exposed at the gap 22. As an example, the nucleotide bases 24 exposed at the gap 22 may be G-G-G-G-G-G-G, and the switch strand 28A may be C-C-C-C-C-C-C. As another example, the nucleotide bases 24 exposed at the gap 22 may be G-A-G-T-G-C-G-G, and the switch strand 28A may be C-T-C-A-C-G-C-C. In example shown in FIG. 3A, any suitable sequence may be used for the switch strand 28A, as long as it has the same number of bases as, and is completely complementary to, the bases 24 exposed at the gap 22. An example of the labeled nucleotide 30A including a completely complementary switch strand 28A is shown in FIG. 3A. As depicted, the switch strand 28A of the labeled nucleotide 30A associates itself with the nucleotide bases 24 exposed at the gap 22. More specifically, in this example, each of the nucleotide bases 36 in the switch strand 28A temporarily and at least partially hybridizes to its complementary base 24 (of the polynucleotide chain 20) that is exposed at the gap 22 in the polynucleotide chain 18. In some examples, the hybridization is not complete, and in other examples, the hybridization is complete. To achieve partial or complete hybridization, the melting temperature of the interaction between the complementary bases can be tuned. Different degrees of hybridization between different switch strands 28A and nucleotide bases 24 enables different time signatures to be achieved with different switch strands 28A. When incorporated, the switch strand 28A closes a switch of the modified dsNA 16', which significantly changes (e.g., increases) the conductivity of the dsNA 16', modulates the channel 16, and results in a detectable change.

Figure 3B:
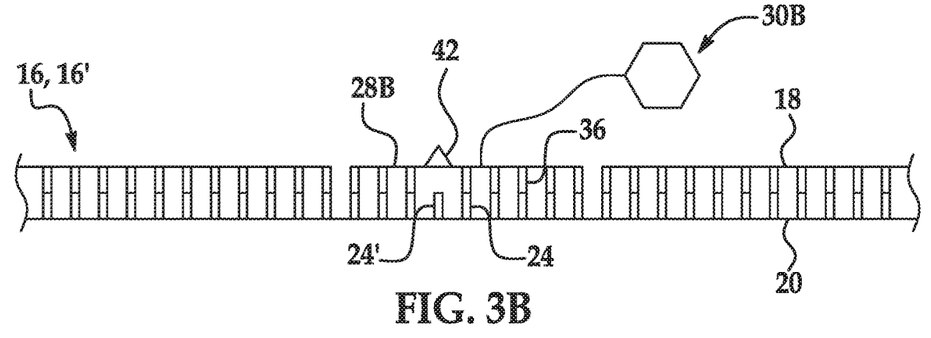

In another example, the bases 36 in the switch strand 28 are not completely complementary to the plurality of nucleotide bases 24 exposed at the gap 22; but rather, the switch strand 28B includes at least one nucleotide having a mismatched base 42 that is non-complementary to a corresponding one (shown as 24') of the plurality of nucleotide bases 24 exposed at the gap 22, as shown in FIG. 3B. In other words, the mismatched base 42 is not complementary to the corresponding nucleotide base 24' exposed at the gap 22. As an example, the nucleotide bases 24 exposed at the gap 22 may be G-G-G-G-G-G-G, and the switch strand 28B may be C-C-C-A-C-C-C. In this example, the adenine of the switch strand 28B is the mismatched base 42 because it is not complementary to the corresponding guanine exposed at the gap 22 of the polynucleotide chain 20. As another example, the nucleotide bases 24 exposed at the gap 22 may be G-A-G-T-G-C-G-G, and the switch strand 28B may be C-C-C-A-C-G-C-C. In this example, the second cytosine of the switch strand 28B is the mismatched base 42 because it is not complementary to the corresponding adenine exposed at the gap 22 of the polynucleotide chain 20. In the example shown in FIG. 3B, any suitable sequence may be used for the switch strand 28B, as long as it has the same number of bases as, is partially complementary to, and includes at least one mismatched base to the bases 24 exposed at the gap 22. As depicted, the switch strand 28B of the labeled nucleotide 30B associates itself with the nucleotide bases 24 exposed at the gap 22. More specifically, in this example, while some of the nucleotide bases 36 in the switch strand 28B temporarily hybridize to respective complementary bases 24, the mismatched base 42 and the corresponding nucleotide base 24' in the polynucleotide chain 20 remain unbound. When incorporated, the switch strand 28B substantially closes a switch of the modified dsNA 16' (but does not fully close the switch due to the mismatched base 42), which significantly changes (e.g., increases) the conductivity of the dsNA, 16', modulates the channel 16, and results in a detectable change. It is to be understood that, in some examples, the conductivity increase with switch strand 28B may not be as large as the increase observed with the switch strand 28A, due to the mismatched base 42.

Figure 3C:
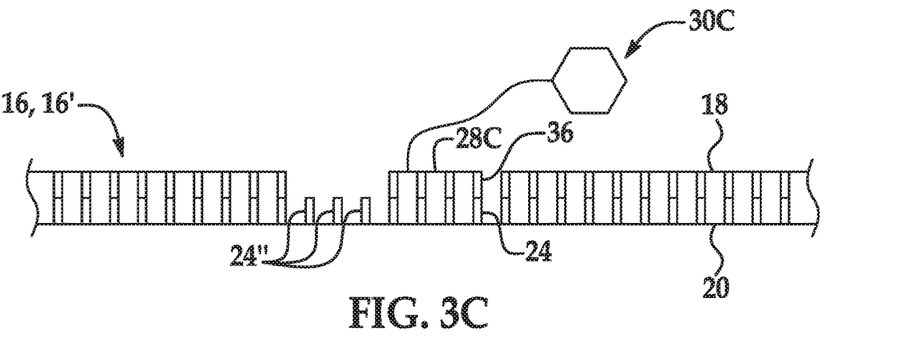

In yet another example, the strand of nucleotides in the switch strand 28 has at least one nucleotide fewer than the plurality of nucleotide bases 24 exposed at the gap 22. An example of this switch strand 28C is shown in FIG. 3C. The nucleotides in the switch strand 28C are complementary to some of the nucleotide bases 24 exposed at the gap 22; however, after the switch strand 28C is associated at the gap 22, at least one of the nucleotide bases 24" remains unbound because of the shorter switch strand length (due to the missing bases). As an example, the nucleotide bases 24 exposed at the gap 22 may be G-G-G-G-G-G-G, and the switch strand 28C may be C-C-C-C-C. In this example, the switch strand 28C is missing two bases, or is two nucleotides shorter than the total number of nucleotide bases 24 (including 24") exposed at the gap 22. As another example, the nucleotide bases 24 exposed at the gap 22 may be G-A-G-T-G-C-G-G, and the switch strand 28C may be T-C-A-C-G-C-C. In this example, the switch strand 28C is missing one base, or is one nucleotide shorter than the total number of nucleotide bases 24 (including 24") exposed at the gap 22. In the example shown in FIG. 3C, any suitable sequence may be used for the switch strand 28C, as long as it has fewer than the total number of bases 24 exposed at the gap 22 and is complementary to some of the bases 24 exposed at the gap 22. As depicted in FIG. 3C, when the switch strand 28C of the labeled nucleotide 30C associates itself at the gap 22, i) the nucleotide bases 36 in the switch strand 28C temporarily and at least partially hybridize to respective complementary bases 24, and ii) some of the nucleotide bases 24" in the polynucleotide chain 20 remain unbound because the switch strand 28 is missing bases. When incorporated, the switch strand 28C substantially closes a switch of the modified dsNA 16' (but does not fully close the switch due to the missing base(s)), which significantly changes (e.g., increases) the conductivity of the modified dsNA 16' (and the channel 16) and results in a detectable change. It is to be understood that, in some examples, the conductivity increase with switch strand 28C may not be as large as the increase observed with the switch strand 28A, due to the missing bases.

Figure 3D:
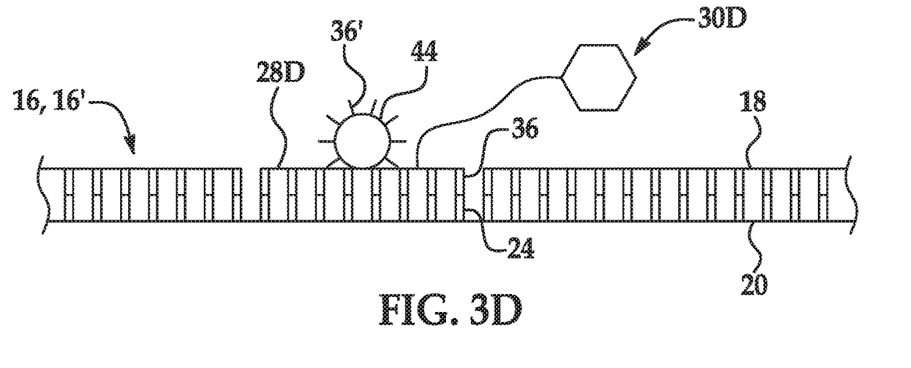

In still another example, the strand of nucleotides in the switch strand 28 has a higher number of nucleotides than the plurality of nucleotide bases 24 exposed at the gap 22, and a portion of the switch strand 28 forms a stem loop when associated at the gap 22. An example of this switch strand 28D is shown in FIG. 3D. Some of the nucleotides in the switch strand 28D are complementary to the nucleotide bases 24 exposed at the gap 22; however, after the switch strand 28D is associated at the gap 22, non-complementary nucleotides 36' of the switch strand 28C remain unbound and form the stem loop 44. As an example, the nucleotide bases 24 exposed at the gap 22 may be G-G-G-G-G-G-G-G-G, and the switch strand 28C may be C-C-C-C. In this example, the switch strand 28D includes nine additional bases 36' that forms a stem loop 44. As another example, the nucleotide bases 24 exposed at the gap 22 may be A-G-T-T-T-T-T-T-G, and the switch strand 28C may be T-C-C. In this example, the switch strand 28C includes six additional bases 36' that forms a stem loop 44. In the example shown in FIG. 3D, any suitable sequence may be used for the switch strand 28C, as long as it has more than the total number of bases 24 exposed at the gap 22 and includes at least some nucleotide bases that are complementary to the bases 24 exposed at the gap 22. The nucleotide bases at either end of the stem loop 44 may be completely complementary to the nucleotide bases 24 exposed at the gap 22, may include one or more non-complementary bases, may have missing bases, or may include combinations of complementary, non-complementary, and missing bases. As depicted in FIG. 3D, when the switch strand 28D of the labeled nucleotide 30D associates itself at the gap 22, i) some of the nucleotide bases 36 in the switch strand 28D temporarily and at least partially hybridize to respective complementary bases 24, and ii) some of the non-complementary nucleotide bases 36" in the switch strand 28D remain unbound and form the stem loop 44. When incorporated, the switch strand 28D closes a switch of the modified dsNA 16', which significantly changes (e.g., increases) the conductivity of the modified dsNA 16', modulates the channel 16, and results in a detectable change. Some of the electronic current is going to be carried on either chain 18, 20 (e.g., when both chains 18, 20 are bound to the electrodes 12, 14), so adding a stem loop 44 is comparable to adding a larger resistor in parallel.

Any example of the labeled nucleotides 30 (e.g., 30A, 30B, 30C, 30D) disclosed herein may be used in a reagent solution of an example of the kit, and/or in a sensing system 40, 40', examples of which is shown in FIGS. 4 and 5. Each of the systems 40, 40' also includes an example of the sensor 10 disclosed herein.

The example of the sensing system 40 shown in FIG. 4 includes a flow cell 41 and an electronic sensor 10 integrated into the flow cell 41. The electronic sensor 10 includes two electrodes 12, 14; a modified, partially double stranded nucleic acid polymer 16 bridging the two electrodes 12, 14, the modified, partially double stranded nucleic acid polymer 16 including two polynucleotide chains 18, 20 partially bonded (via hydrogen bonding) together, a gap 22 in a first 18 of the polynucleotide chains wherein nucleotides are missing; and a plurality of nucleotide bases 24 of a second 20 of the polynucleotide chains exposed at the gap 22. The flow cell 41 is a vessel that contains the sensor 10. It is to be understood that other vessels, such as a well, tube, channel, cuvette, Petri plate, bottle, or the like may alternatively contain the sensor 10. Cyclic processes, such as nucleic acid sequencing reactions, are particularly well suited for flow cells 41.

Example flow cells 41 include a substrate/support 13 and a lid 43 bonded directly or indirectly thereto or integrally formed therewith. Flow cell 41 may include a fluid inlet 45 and a fluid outlet 47 that enable delivery of bulk reagents to one sensor 10 or an array of sensors 10 contained within the flow cell 41.

The sensing system 40 may also include a reagent delivery system 49 to selectively introduce a reagent to an input (e.g., fluid inlet 45) of the flow cell 41, over the sensor 10, and then out of the fluid outlet 47. The reagent delivery system 49 may include tubing or other fluidics that can permanently or removably attach to the fluid inlet 45. The reagent deliver system 49 may include a sample container 51. The reagent (including the labeled nucleotide 30 to be introduced to the electronic sensor 10) may be stored in the sample container or prepared and introduced to the sample container just before use. The reagent deliver system 49 may also include a pump or other suitable equipment to retrieve the reagent from the sample container 51 and deliver it to the fluid inlet 45. In other examples, the sample container 51 is positioned so the reagent can flow by gravity to the fluid inlet 45, over the sensor 10, and out the fluid outlet 47.

The sensor 10 in the flow cell 41 may also be operatively connected to a detector 15 to detect conductivity changes of the sensor 10 when the sensing system 40 is used.

Another example of the system 40' is shown in FIG. 5 and includes an electronic sensor 10, which includes two electrodes 12, 14; a modified, partially double stranded nucleic acid polymer 16 bridging the two electrodes 12, 14, the modified, partially double stranded nucleic acid polymer 16 including two polynucleotide chains 18, 20 partially bonded (via hydrogen bonding) together, a gap 22 in a first 18 of the polynucleotide chains wherein nucleotides are missing; and a plurality of nucleotide bases 24 of a second 20 of the polynucleotide chains exposed at the gap 22; and separate reagents that are to be introduced to the electronic sensor 10, the reagents including labeled nucleotides 30, at least one of the labeled nucleotides 30 including a nucleotide 32, a linking molecule 34 attached to a phosphate group of the nucleotide, a switch strand 28 attached to the linking molecule 34, the switch strand 28 including a strand of nucleotides including bases 36 complementary to at least some of the plurality of nucleotide bases 24 exposed at the gap 22. In the example shown in FIG. 5, the polynucleotide chain 18 is ACCGGGGTA-gap-ATCCG and the polynucleotide chain 20 is TGGGCCCCATCCCCCCTAGGC (SEQ. ID No. 1). In the polynucleotide chain 20, the nucleotide bases "CCCCCC" are exposed at the gap 22 (at least until a switch strand 28 is associated therewith).

While not shown, it is to be understood that the sensor 10 may be positioned within or part of a vessel, such as flow cell 41 (FIG. 4), a tube, channel, cuvette, Petri plate, bottle, or the like. Another example of a suitable vessel is a flow cell.

While one sensor 10 is shown in FIG. 5, it is to be understood that the sensing system 40' may include an array of sensors 10 positioned on a substrate. Moreover, the sensor(s) 10 of the sensing system 40' may each be electrically connected to a respective detector 15 to detect a response from the electrical sensor 10 when the switch strand 28 is associated at the gap 22.

Some examples of the sensing system 40' further include a polymerase 38 anchored to the modified dsNA 16', and a template polynucleotide chain 48 that is to be introduced to the sensor 10.

As shown in FIG. 5, the sensor 10 includes the polymerase 38. Any DNA polymerase may be used that can catalyze the addition of one nucleotide at a time to the nascent strand. The DNA polymerase may be from any of the following families: A, B, C, D, X, Y, and RT. Specific examples from family A include T7 DNA polymerase, Pol I, Pol γ, Pol Θ, or Pol ν; or from family B include Pol II, Pol B, Pol ζ, Pol α, Pol δ, and Pol ε; or from family C include Pol III; or from family D include Pol D (DP1/DP2 heterodimer), or from family X include Pol β, Pol α, Pol λ, Pol μ, and Terminal deoxynucleotidyl transferase; or from family Y include Pol ι, Pol κ, Pol η, Pol IV, and Pol V; or from family RT include Telomerase.

As shown in FIG. 5, the polymerase 38 is immobilized to the modified dsNA 16' with a tether 46. In another example, the polymerase 38 is immobilized to a substrate with the tether 46. The tether 46 is used as an anchor for the polymerase 38, and it may be desirable that the tether 46 be non-conducting. A non-conducting tether may be particularly desirable when the polymerase 38 is attached to the modified dsNA 16'. Examples of a suitable tether 46 includes polyethylene glycol (PEG) with a cleavable link at some point along the PEG chain, or may include Nickel NTA/His tag chemistry, streptavidin/biotin chemistry (e.g., streptavidin attached to the modified dsNA 16' and biotin attached to the polymerase 38), DNA-DNA hybridization, DNA-PNA hybridization, carboxyl silane 1-ethyl-3-(3-dimethylaminopropyl)carbodiimide (EDC), or any other suitable linker that can attach the polymerase to the modified dsNA 16' or to the substrate surface. In some examples, the tether 46 holds the polymerase 38 at least 10 nm away from the modified dsNA 16'. This may be desirable, for example, so that conformal changes to the polymerase 38, charges of the polymerase 38, and/or charges of the target/template polynucleotide chain 48 held by the polymerase 38 do not interfere with the sensing operation of the modified dsNA 16'.

In an example, the modified dsNA 16' may be initially attached to the polymerase 38 by the tether 46, which includes a cleavable link. This combination may be introduced to the electrodes 12, 14 to attach the opposed ends of the modified dsNA 16' to the electrodes 12, 14 and to attach the polymerase 38 to a substrate surface via, e.g., Nickel NTA/His tag chemistry. In this example, the cleavable link may be cleaved to detach the polymerase 38 from the modified dsNA 16'. In this example, the polymerase 38 is in proximity to the modified dsNA 16', but is not actually touching it. It is to be understood that the tether 46 may be cleaved when chemistry is provided to hold the polymerase 38, e.g., on the substrate surface and within proximity to the sensor 10.

As mentioned herein, examples of the system 40, 40' may also include the template polynucleotide chain 48 that is to be introduced to the sensor 10.

The template polynucleotide chain 48 may be any sample that is to be sequenced, and may be composed of DNA, RNA, or analogs thereof (e.g., peptide nucleic acids). The source of the template (or target) polynucleotide chain 48 can be genomic DNA, messenger RNA, or other nucleic acids from native sources. In some cases, the template polynucleotide chain 48 that is derived from such sources can be amplified prior to use in a method or system 40, 40' herein. Any of a variety of known amplification techniques can be used including, but not limited to, polymerase chain reaction (PCR), rolling circle amplification (RCA), multiple displacement amplification (MDA), or random primer amplification (RPA). It is to be understood that amplification of the template polynucleotide chain 48 prior to use in the method or system 40, 40' set forth herein is optional. As such, the template polynucleotide chain 48 will not be amplified prior to use in some examples. Template/target polynucleotide chains 48 can optionally be derived from synthetic libraries. Synthetic nucleic acids can have native DNA or RNA compositions or can be analogs thereof.

Biological samples from which the template polynucleotide chain 48 can be derived include, for example, those from a mammal, such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *Dictyostelium discoideum*; a fungi such as *Pneumocystis carinii Takifugu rubripes*, yeast, *Saccharamoyces cerevisiae* or *Schizosaccharomyces pombe*; or a *Plasmodium falciparum*. Template polynucleotide chains 48 can also be derived from prokaryotes such as a bacterium, *Escherichia coli*, staphylococci or *Mycoplasma pneumoniae*; an archae; a virus such as Hepatitis C virus, ebola virus or human immunodeficiency virus; or a viroid. Template polynucleotide chains 48 can be derived from a homogeneous culture or population of the above organisms or alternatively from a collection of several different organisms, for example, in a community or ecosystem.

Moreover, template polynucleotide chains 48 may not be derived from natural sources, but rather can be synthesized using known techniques. For example, gene expression probes or genotyping probes can be synthesized and used in the examples set forth herein.

In some examples, template polynucleotide chains 48 can be obtained as fragments of one or more larger nucleic acids. Fragmentation can be carried out using any of a variety of techniques known in the art including, for example, nebulization, sonication, chemical cleavage, enzymatic cleavage, or physical shearing. Fragmentation may also result from use of a particular amplification technique that produces amplicons by copying only a portion of a larger nucleic acid chain. For example, PCR amplification produces fragments having a size defined by the length of the nucleotide sequence on the original template that is between the locations where flanking primers hybridize during amplification. The length of the template polynucleotide chain 48 may be in terms of the number of nucleotides or in terms of a metric length (e.g., nanometers).

A population of template/target polynucleotide chains 48, or amplicons thereof, can have an average strand length that is desired or appropriate for a particular application of the methods or system 40, 40' set forth herein. For example, the average strand length can be less than about 100,000 nucleotides, about 50,000 nucleotides, about 10,000 nucleotides, about 5,000 nucleotides, about 1,000 nucleotides, about 500 nucleotides, about 100 nucleotides, or about 50 nucleotides. Alternatively or additionally, the average strand length can be greater than about 10 nucleotides, about 50 nucleotides, about 100 nucleotides, about 500 nucleotides, about 1,000 nucleotides, about 5,000 nucleotides, about 10,000 nucleotides, about 50,000 nucleotides, or about 100,000 nucleotides. The average strand length for a population of target polynucleotide chains 48, or amplicons thereof, can be in a range between a maximum and minimum value set forth above.

In some cases, a population of template/target polynucleotide chains 48 can be produced under conditions or otherwise configured to have a maximum length for its members. For example, the maximum length for the members can be less than about 100,000 nucleotides, about 50,000 nucleotides, about 10,000 nucleotides, about 5,000 nucleotides, about 1,000 nucleotides, about 500 nucleotides, about 100 nucleotides or about 50 nucleotides. Alternatively or additionally, a population of template polynucleotide chains 48, or amplicons thereof, can be produced under conditions or otherwise configured to have a minimum length for its members. For example, the minimum length for the members can be more than about 10 nucleotides, about 50 nucleotides, about 100 nucleotides, about 500 nucleotides, about 1,000 nucleotides, about 5,000 nucleotides, about 10,000 nucleotides, about 50,000 nucleotides, or about 100,000 nucleotides. The maximum and minimum strand length for template polynucleotide chains 48 in a population can be in a range between a maximum and minimum value set forth above.

As shown in FIG. 5, the template polynucleotide chain 48 (e.g., a single stranded DNA strand) to be sequenced is bound to the polymerase 38 after having been introduced in solution along with reagents, such as the labeled nucleotides 30.

In some examples, several different labeled nucleotides 30 (e.g., respectively labeled with dA, dC, dG, and dT as the nucleotide 32) may be used together in a system 40, 40' including an array of sensors 10. In one example, four different labeled nucleotides 30 are used, each including a different nucleotide 32 and a different nucleotide-specific switch strand 28. As an example, the labeled nucleotides 30 include a first labeled nucleotide, which includes deoxyadenosine polyphosphate as the nucleotide and a first nucleotide-specific switch strand; a second labeled nucleotide, which includes deoxyguanosine polyphosphate as the nucleotide and a second nucleotide-specific switch strand having a different sequence than the first switch strand; a third labeled nucleotide, which includes deoxycytidine polyphosphate as the nucleotide and a third nucleotide-specific switch strand having a different sequence than each of the first and second switch strands; and a fourth labeled nucleotide, which includes deoxythymidine polyphosphate as the nucleotide and a fourth nucleotide-specific switch strand having a different sequence than each of the first, second, and third switch strands. As such, in this example, the first, second, third, and fourth nucleotide-specific switch strands are different from each other. The different switch strands will generate different conductivity changes (when associated at a complementary gap 22), which may be used to identify the specific nucleotide attached thereto.

Figure 6:
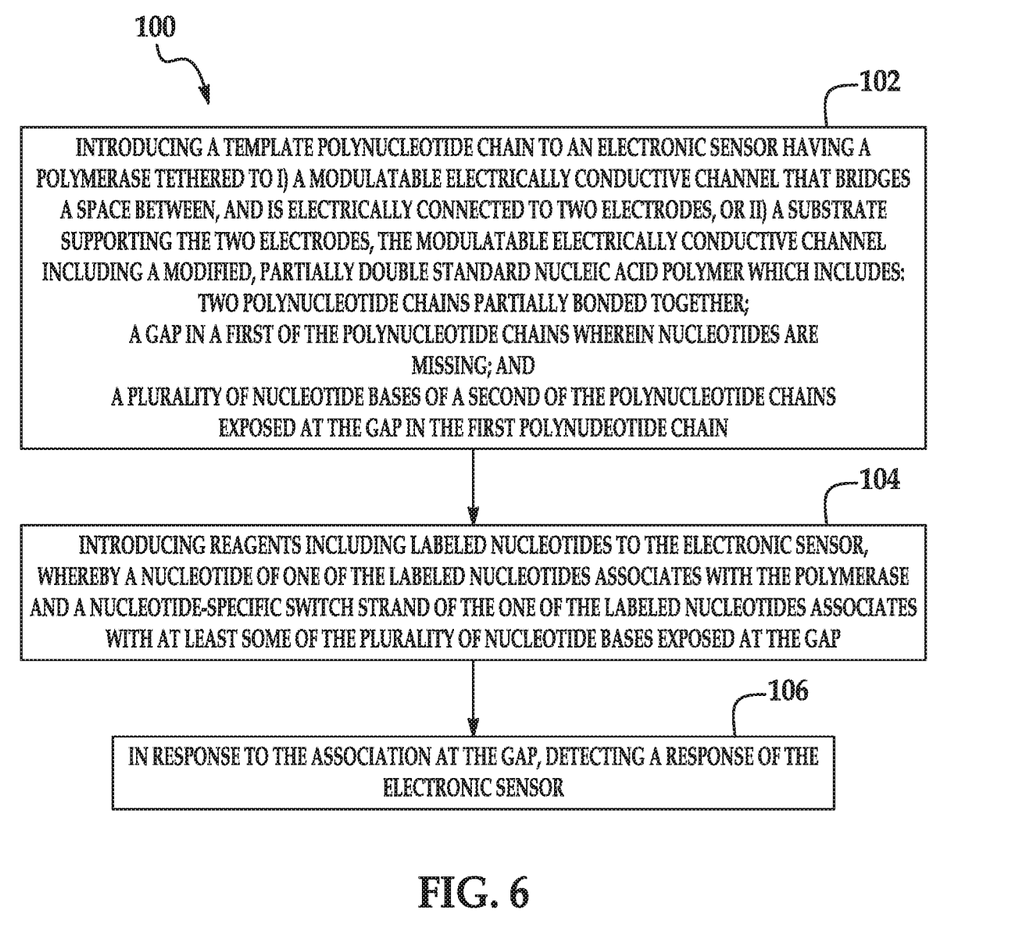
FIG. 6 is a flow diagram of an example of a method disclosed herein.

Referring now to FIG. 6, an example of a method is depicted. The method 100 includes introducing a template polynucleotide chain 48 to an electronic sensor 10 having a polymerase 38 tethered to i) a modulatable electrically conductive channel 16 that bridges a space between, and is electrically connected to two electrodes 12, 14, or ii) a substrate 13 supporting the two electrodes 12, 14, the modulatable electrically conductive channel 16 including a modified, partially double stranded nucleic acid polymer 16', which includes: two polynucleotide chains 18, 20 partially bonded together; a gap 22 in a first of the polynucleotide chains 18 wherein nucleotides are missing; and a plurality of nucleotide bases 24 of a second of the polynucleotide chains 20 exposed at the gap 22 in the first of the polynucleotide chains 18 (reference numeral 102); introducing reagents including labeled nucleotides 30 to the electronic sensor 10, whereby a nucleotide 32 of one of the labeled nucleotides 30 associates with the polymerase 38 and a nucleotide-specific switch strand 28 of the one of the labeled nucleotides 30 associates with at least some of the plurality of nucleotide bases 24 exposed at the gap 22 (reference numeral 104); and in response to the association at the gap 22, detecting a response of the electronic sensor 10. FIG. 5 will also be referenced throughout the discussion of the method 100.

As shown in FIG. 5, the template polynucleotide chain 48 introduced to the sensor 10 may be held in place by the polymerase 38, which is tethered to the sensor 10 or to a substrate surface that supports the sensor 10. The template polynucleotide chain 48 shown in FIG. 5 is a template strand of DNA. The template polynucleotide chain 48 may be introduced in a biologically stable solution, along with reagents, such as the labeled nucleotides 30. The biologically stable solution may be any buffer suitable for polymerase base incorporation reactions, such as polymerase chain reaction (PCR) or linear amplification. As an example, biologically stable solution may include a buffer having a pH near 7, a salt concentration above several millimolar, and $Mg^{2+}$ ions at millimolar concentration.

Also as shown in FIG. 5, the labeled nucleotide 30 may include a base that is complementary to a target nucleic acid of the template polynucleotide chain 48. The labeled nucleotide 30 will be held in place, in part, by the polymerase 38 that is also bound to the template polynucleotide chain 48.

The interaction between the labeled nucleotide 30 and polymerase 38 and the length of the linking molecule 34 enable the switch strand 28 to associate with the gap 22 of the sensor 10. In an example, the association of the switch strand 28 with the gap 22 involves hybridization of at least a portion of the switch strand 28 with the nucleotide bases 24 exposed at the gap 22. The hybridization that takes place will depend, in part, upon the switch strand 28 (e.g., 28A, 28B, 28C, 28D) that is used. The temperature and/or ion concentration of the solution may be adjusted in order to initiate or promote the complete or partial hybridization or annealing of the switch strand 28 to at least some of the nucleotide bases 24 exposed at the gap 22. As one example, the switch strand 28 may be designed to partially or completely hybridize at the gap 22 at room temperature (e.g., from about 18° C. to about 22° C.) and in a solution having a 50 mM salt concentration.

The polymerase 38 will hold the switch strand 28 in proximity to the gap 22, thus allowing several hybridization and de-hybridization events to occur. In contrast, a random strand drifting by will likely hybridize once and then drift away. The switch strand 28 may be held in proximity to the gap 22 until it is disassociated, for example, using melting or another suitable technique. In some instances, the association of the switch strand in the gap 22 may be up to tens of milliseconds, or longer. This relatively long interaction turns the switch "ON" (e.g., modulate the channel 16 by increasing the conductance from the lower state) and the change in conductivity can be detected. This relatively long interaction is unlike other labeled nucleotides 30 present in the solution (i.e., the random, drifting strand), which may diffuse and briefly touch, but not undergo several at least partial hybridization and de-hybridization events at the sensor 10. The brief interaction of these other labeled nucleotides 30 may cause a short-lived and/or sporadic conductivity change, and thus is distinguishable from the conductivity change that results from the switch strand 28 being held in proximity to the gap 22.

When the switch strand 28 does at least partially hybridize and de-hybridize several times to the exposed nucleotide bases 24, the response of the sensor 10 may be indicative of the base of the labeled nucleotide 30 because the switch strand 28 is nucleotide-specific (i.e., a specific switch strand 28 is selected for a specific base). As such, the method 100 may also involve associating the response of the sensor 10 with the associated nucleotide-specific switch strand 28 (i.e., the labeled nucleotide 30 that has associated with the polymerase 38 and the gap 22), and based on the nucleotide-specific switch strand 28, identifying the nucleotide (e.g., the base) of the associated labeled nucleotide 30 (i.e., the labeled nucleotide 30 that has associated with the polymerase 38 and the gap 22).

The base of the associated labeled nucleotide 30 will be incorporated into a nascent strand 50 that is hybridized to the template polynucleotide chain 48. This will, in turn, break the bond between the phosphate group(s) of the labeled nucleotide 30 and the newly incorporated nucleotide base. This cleaves the remainder of the labeled nucleotide 30 from the newly incorporated nucleotide base.

Since the switch strand 28 may prefer to be at least partially hybridized and stay connected in the double helix configuration of the modified dsNA 16', the method 100 may further involve heating to disassociate the nucleotide-specific switch strand 28 from the gap 22. The melting temperature of the switch strand 28 may be tuned when synthesizing the labeled nucleotide 30 to make the "ON" time shorter or longer, depending, in part, on how long the polymerase 38 holds the nucleotide 32 of the labeled nucleotide 30. In an example, the melting temperature may be tuned to correspond with the temperature at which the sensing system 40, 40' is operated when the bond between the phosphate group(s) of the labeled nucleotide 30 and the newly incorporated nucleotide base. This would cause the dissociation of the switch strand 28 within the same time frame of when the labeled nucleotide 30 is cleaved. In another example, it may be desirable for the "OFF" time of the switch strand 28 to be much shorter than the time that the labeled nucleotide 30 is held by the polymerase 28 during incorporation into the nascent strand 50. This may minimize background events from the switch strands 28 that are not associated with the polymerase 28.

As a result of cleavage and disassociation, the remainder of the labeled nucleotide 30 is free to dissociate from the nucleotide base and diffuse away from the sensor 10. Cleavage and disassociation again modulates the channel 16, by returning the conductivity of the sensor 10 to the initial (e.g., lower) conductivity state it was in before the association of the labeled nucleotide 30 with the polymerase 38 and with the gap 22. The appearance and disappearance of signal as the conductivity of the sensor 10 changes (e.g., increases and returns to the lower state), respectively, can be correlated with the incorporation of a nucleotide base into the nascent strand 50 of the template nucleotide chain 48 and the subsequent dissociation of the labeled nucleotide 30.

In the example method 100, the associating of the one of the labeled nucleotides 30 (with the polymerase 32 and the gap 22), the detecting, the associating of the response, and the identifying together may be used for single molecule detection of a polymerase incorporation event (i.e., which nucleotide has been incorporated into the nascent strand 50).

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

The terms "substantially" and "about" used throughout this disclosure, including the claims, are used to describe and account for small fluctuations, such as due to variations in processing. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

Furthermore, it is to be understood that the ranges provided herein include the stated range and any value or sub-range within the stated range, as if they were explicitly recited. For example, a range represented by from about 10 nm to about 50 nm, should be interpreted to include not only the explicitly recited limits of from about 10 nm to about 50 nm, but also to include individual values, such as about 15 nm, 22.5 nm, 45 nm, etc., and sub-ranges, such as from about 20 nm to about 48 nm, etc.

While several examples have been described in detail, it is to be understood that the disclosed examples may be modified. Therefore, the foregoing description is to be considered non-limiting.

---

---

What is claimed is:

1. A sensor, comprising:
two electrodes having a space therebetween;
a modulatable electrically conductive channel attached to the two electrodes, the modulatable electrically conductive channel including a modified, partially double stranded nucleic acid polymer electrically connected to the two electrodes and bridging the space between the two electrodes, the modified, partially double stranded nucleic acid polymer including:
a first polynucleotide chain and a second polynucleotide chain partially bonded together;

a gap in the first polynucleotide chain wherein nucleotides are missing, the gap configured to at least partially receive the switch strand; and a plurality of nucleotide bases of the second polynucleotide chain exposed at the gap in the first polynucleotide chain; and a polymerase immobilized, via a tether, to the modified, partially double stranded nucleic acid polymer.

2. The sensor as defined in claim 1, wherein the gap has a length ranging from about 10 nm to about 50 nm.

3. The sensor as defined in claim 1, wherein at least one of the plurality of nucleotide bases exposed at the gap is a guanine base.

4. The sensor as defined in claim 1, wherein each of the plurality of nucleotide bases exposed at the gap is a guanine base.

5. The sensor as defined in claim 1, further comprising a detector to detect a response from the modified, partially double stranded nucleic acid polymer when a switch strand, including a strand of nucleotides including bases complementary to at least some of the plurality of nucleotide bases exposed at the gap, associates with the at least some of the plurality of nucleotide bases at the gap.

6. The sensor as defined in claim 1, further comprising a fluidic system including a fluid inlet to introduce a reagent to the modified, partially double stranded nucleic acid polymer.

7. The sensor as defined in claim 6, wherein the fluid inlet of the fluidic system is attached to a reagent delivery system to introduce the reagent to the fluid inlet, wherein the reagent delivery system includes a sample container and the reagent stored in the sample container, and wherein the reagent includes labeled nucleotides, at least one of the labeled nucleotides including:
a nucleotide;
a linking molecule attached to a phosphate group of the nucleotide; and
a switch strand attached to the linking molecule, the switch strand including a strand of nucleotides including bases complementary to at least some of the plurality of nucleotide bases exposed at the gap.

8. The sensor as defined in claim 1, further comprising a plurality of other modulatable electrically conductive channels attached to the two electrodes, each of the other modulatable electrically conductive channels including a respective modified, partially double stranded nucleic acid polymer electrically connected to the two electrodes and bridging the space between the two electrodes.

9. The sensor as defined in claim 1 wherein, the modulatable electrically conductive channel exhibits:
a first conductance when the plurality of nucleotide bases are exposed at the gap; and
a second conductance that is different than the first conductance when at least some of the plurality of nucleotide bases at the gap are associated with complementary nucleotide bases.

10. The sensor as defined in claim 1, further comprising a labeled nucleotide comprising:
a nucleotide;
a linking molecule attached to a phosphate group of the nucleotide; and
a switch strand attached to the linking molecule, the switch strand including a strand of nucleotides including bases complementary to at least some of the plurality of nucleotide bases exposed at the gap of the sensor of claim 1.

11. The sensor as defined in claim 1, wherein the tether is selected from the group consisting of a polyethylene glycol with a cleavable link, Nickel NTA/His tag chemistry, streptavidin/biotin chemistry, DNA-DNA hybridization, DNA-PNA hybridization, and carboxyl silane 1-ethyl-3-(3-dimethylaminopropyl)carbodiimide.

12. The sensor as defined in claim 1, wherein the tether holds the polymerase at least 10 nm away from the modified, partially double stranded nucleic acid polymer.

13. A sensing system, comprising:
a flow cell; and
an electronic sensor integrated into the flow cell, the electronic sensor including:
two electrodes having a space therebetween;
a modulatable electrically conductive channel attached to the two electrodes, the modulatable electrically conductive channel including a modified, partially double stranded nucleic acid polymer electrically connected to the two electrodes and bridging the space between the two electrodes, the modified, partially double stranded nucleic acid polymer including:
a first polynucleotide chain and a second polynucleotide chain partially bonded together;
a gap in the first polynucleotide chain wherein nucleotides are missing, the gap configured to at least partially receive the switch strand; and
a plurality of nucleotide bases of the second polynucleotide chain exposed at the gap in the first polynucleotide chain; and
a polymerase immobilized, via a tether, to the modified, partially double stranded nucleic acid polymer.

14. The sensing system as defined in claim 13, further comprising a reagent delivery system to selectively introduce a reagent to an input of the flow cell.

15. The sensing system as defined in claim 14, wherein the reagent is in a sample container, and the reagent includes labeled nucleotides, at least one of the labeled nucleotides including:
a nucleotide;
a linking molecule attached to a phosphate group of the nucleotide; and
a switch strand attached to the linking molecule, the switch strand including a strand of nucleotides including bases complementary to at least some of the plurality of nucleotide bases exposed at the gap.

16. The sensing system as defined in claim 13, further comprising a detector to detect a response from the electronic sensor.

17. A method, comprising:
introducing a template polynucleotide chain to an electronic sensor having a polymerase immobilized, via a tether to a modulatable electrically conductive channel that bridges a space between, and is electrically connected to two electrodes, the modulatable electrically conductive channel including a modified, partially double stranded nucleic acid polymer, which includes:
a first polynucleotide chain and a second polynucleotide chain partially bonded together;
a gap in the first polynucleotide chain wherein nucleotides are missing, the gap configured to at least partially receive the switch strand; and
a plurality of nucleotide bases of the second polynucleotide chain exposed at the gap in the first polynucleotide chain;
introducing reagents including labeled nucleotides to the electronic sensor, whereby a nucleotide of one of the labeled nucleotides associates with the polymerase and a nucleotide-specific switch strand of the one of the labeled nucleotides associates with at least some of the plurality of nucleotide bases exposed at the gap; and in response to the association at the gap, detecting a response of the electronic sensor.

18. The method as defined in claim 17, further comprising:
    associating the response of the electronic sensor with the associated nucleotide-specific switch strand; and
    based on the associated nucleotide-specific switch strand, identifying the nucleotide of the one of the labeled nucleotides.

19. The method as defined in claim 17, further comprising heating to disassociate the nucleotide-specific switch strand from the gap.

* * * * *